United States Patent
Nishigaki et al.

(10) Patent No.: US 10,337,976 B2
(45) Date of Patent: Jul. 2, 2019

(54) MICROANALYSIS CHIP

(71) Applicant: KABUSHIKI KAISHA TOSHIBA, Minato-ku, Tokyo (JP)

(72) Inventors: Michihiko Nishigaki, Kawasaki Kanagawa (JP); Yutaka Onozuka, Yokohama Kanagawa (JP); Kentaro Kobayashi, Tokyo (JP); Hiroshi Hamasaki, Hiratsuka Kanagawa (JP); Naofumi Nakamura, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 327 days.

(21) Appl. No.: 14/732,399

(22) Filed: Jun. 5, 2015

(65) Prior Publication Data
US 2016/0153935 A1 Jun. 2, 2016

(30) Foreign Application Priority Data

Nov. 28, 2014 (JP) .................................. 2014-241519

(51) Int. Cl.
*B01L 3/00* (2006.01)
*G01N 15/00* (2006.01)
(Continued)

(52) U.S. Cl.
CPC ..... *G01N 15/1031* (2013.01); *G01N 15/0266* (2013.01); *G01N 15/0272* (2013.01);
(Continued)

(58) Field of Classification Search
CPC ........... G01N 15/1031; G01N 15/0266; G01N 15/0272; G01N 15/1459;
(Continued)

(56) References Cited

U.S. PATENT DOCUMENTS 6,537,437 B1 * 3/2003 Galambos ............ B01J 19/0093
204/600
2004/0023273 A1 * 2/2004 Puget ................ B01L 3/502761
435/6.19
(Continued)

FOREIGN PATENT DOCUMENTS

JP         11337521 A   12/1999
JP     2008005749 A    1/2008
(Continued)

OTHER PUBLICATIONS

Liang, Xiaogan, and Stephen Y. Chou. "Nanogap detector inside nanofluidic channel for fast real-time label-free DNA analysis." Nano letters 8.5 (2008): 1472-1476.*

*Primary Examiner* — Robert J Eom
(74) *Attorney, Agent, or Firm* — Holtz, Holtz & Volek PC

(57) ABSTRACT

According to one embodiment, a microanalysis chip includes a substrate, a flow channel in which a sample liquid is allowed to flow, the flow channel being provided on a main surface side of the substrate, a reservoir in which the sample liquid is allowed to be stored, the reservoir being provided on a main surface of the substrate, including a bank having a go-around shape and further including a liquid introduction inlet for connection to an end of the flow channel, the liquid introduction inlet being provided on the main surface of the substrate in the bank, and a filter which is provided between the liquid introduction inlet and the end of the flow channel and includes a first micropore for allowing passage of a fine particle in the sample liquid.

6 Claims, 12 Drawing Sheets

(51) Int. Cl.
*G01N 15/02* (2006.01)
*G01N 15/10* (2006.01)
*G01N 15/14* (2006.01)

(52) U.S. Cl.
CPC .... *G01N 15/1459* (2013.01); *B01L 3/502761* (2013.01); *B01L 2200/0668* (2013.01); *B01L 2300/042* (2013.01); *B01L 2300/069* (2013.01); *B01L 2300/0645* (2013.01); *B01L 2300/0681* (2013.01); *B01L 2300/0864* (2013.01); *B01L 2300/0867* (2013.01); *B01L 2300/0896* (2013.01); *B01L 2400/0406* (2013.01); *G01N 2015/0053* (2013.01); *G01N 2015/0065* (2013.01); *G01N 2015/1087* (2013.01); *G01N 2015/1493* (2013.01)

(58) Field of Classification Search
CPC ... G01N 2015/0053; G01N 2015/0065; G01N 2015/1087; G01N 2015/1493; B01L 3/502761; B01L 2200/0668; B01L 2300/042; B01L 2300/0645; B01L 2300/0681; B01L 2300/069; B01L 2300/0864; B01L 2300/0867; B01L 2300/0896; B01L 2400/0406
See application file for complete search history.

(56) References Cited

U.S. PATENT DOCUMENTS

| | | |
|---|---|---|
| 2008/0003678 A1 | 1/2008 | Hattori et al. |
| 2013/0341265 A1 | 12/2013 | Grolla et al. |
| 2014/0252505 A1 | 9/2014 | Kobayashi et al. |
| 2014/0255911 A1 | 9/2014 | Hongo et al. |
| 2014/0256028 A1 | 9/2014 | Kobayashi et al. |
| 2014/0256031 A1 | 9/2014 | Kobayashi et al. |
| 2015/0041316 A1 | 2/2015 | Miki et al. |

FOREIGN PATENT DOCUMENTS

| | | |
|---|---|---|
| JP | 2011208985 A | 10/2011 |
| JP | 2013542445 A | 11/2013 |
| JP | 2014173935 A | 9/2014 |
| JP | 2015099031 A | 5/2015 |
| WO | 2015072186 A1 | 5/2015 |

\* cited by examiner

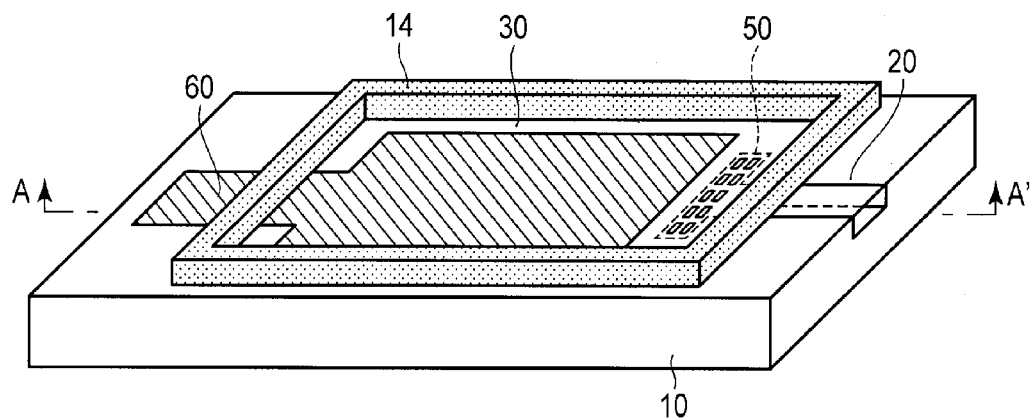
F I G. 1
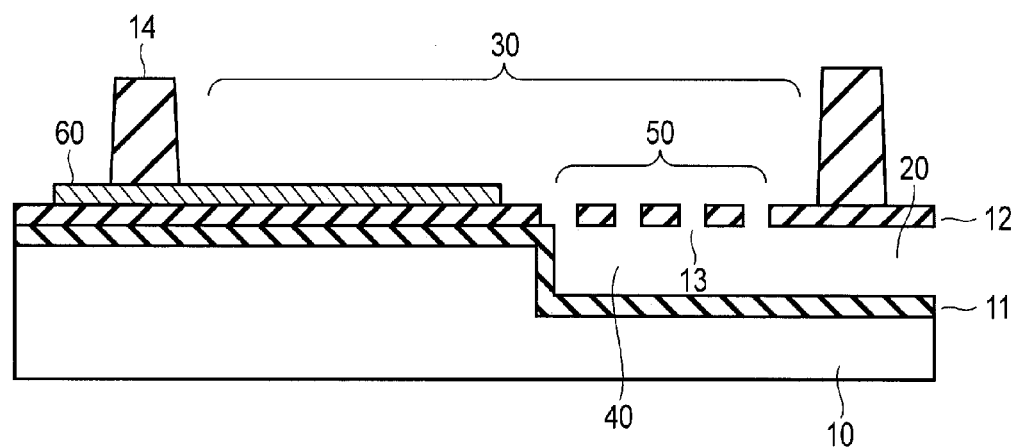
F I G. 2

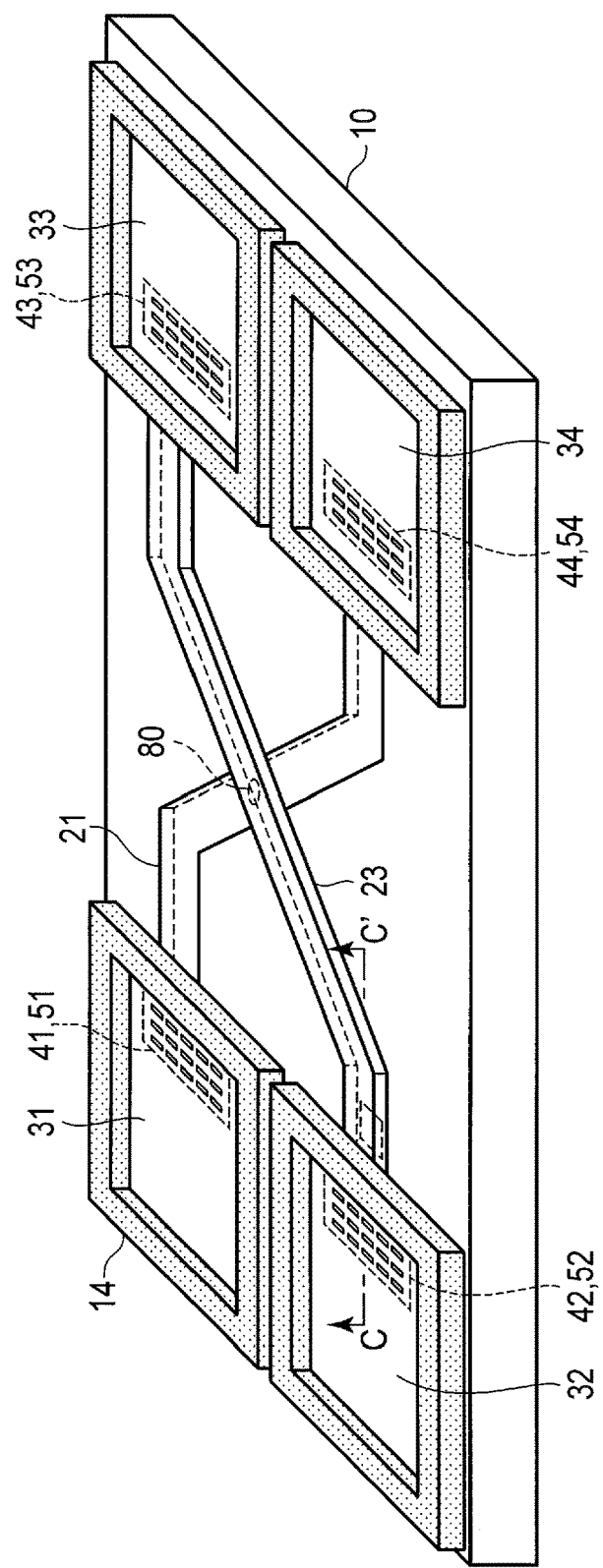
F I G. 5

MICROANALYSIS CHIP

CROSS-REFERENCE TO RELATED APPLICATIONS

This application is based upon and claims the benefit of priority from Japanese Patent Application No. 2014-241519, filed Nov. 28, 2014, the entire contents of which are incorporated herein by reference.

FIELD

Embodiments described herein relate generally to a microanalysis chip configured to detect fine particles in a sample liquid.

BACKGROUND

Recently, in the field of biotechnology or health care, attention has been paid to a semiconductor microanalysis chip which electrically separates and detects fine particles or biopolymers contained in a sample liquid by using micro fluid elements such as a microflow channel and a detection structure. In particular, a structure which introduces a sample liquid from a reservoir into a microflow channel and lets fine particles through the micropore formed in the microflow channel is effective.

In this type of device, it is necessary to introduce the sample liquid from the reservoir in which the sample liquid is dropped into the microflow channel immediately and continuously. Moreover, since the effect of impurities such as fine particles other than the inspection target is a concern, such impurities are preferably excluded between the reservoir and the detection hole. However, at the moment, this problem is not satisfactorily solved because of various factors.

BRIEF DESCRIPTION OF THE DRAWINGS

FIG. 1 is a perspective view showing the main structure of a semiconductor microanalysis chip according to a first embodiment.

FIG. 2 is a cross-sectional view taken along the arrow A-A' of FIG. 1.

FIG. 5 is a perspective view showing the whole structure of a semiconductor microanalysis chip according to a third embodiment.

DETAILED DESCRIPTION

Figure 3A:
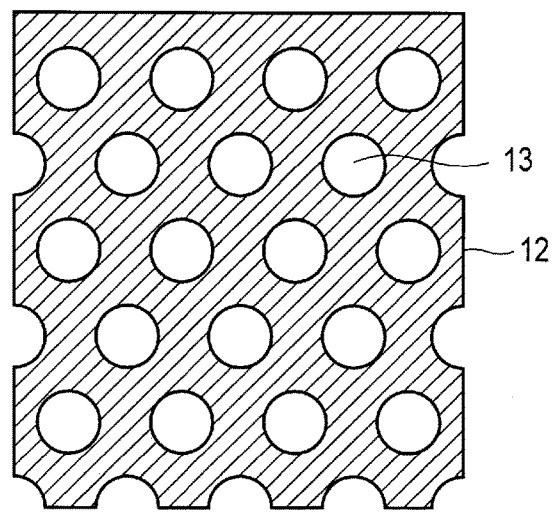
FIGS. 3A to 3C are planar views showing pattern examples of a filter used for the semiconductor microanalysis chip of FIG. 1.

In general, according to one embodiment, a microanalysis chip comprises: a substrate; a flow channel in which a sample liquid is allowed to flow, the flow channel being provided on a main surface side of the substrate; a reservoir in which the sample liquid is allowed to be stored, the reservoir being provided on a main surface of the substrate, comprising a bank having a go-around shape and further comprising a liquid introduction inlet for connection to an end of the flow channel, the liquid introduction inlet being provided on the main surface of the substrate in the bank; and a filter which is provided between the liquid introduction inlet and the end of the flow channel and includes a first micropore for allowing passage of a fine particle in the sample liquid.

Hereinafter, semiconductor microanalysis chips of embodiments will be described with reference to the accompanying drawings.

First Embodiment

FIG. 1 and FIG. 2 are shown for explaining the outline structure of a semiconductor microanalysis chip according to a first embodiment. FIG. 1 is a perspective view showing the structure of a reservoir portion. FIG. 2 is a cross-sectional view taken along the arrow A-A' of FIG. 1.

In the present embodiment, the semiconductor microanalysis chip comprises a semiconductor substrate 10, a microflow channel 20 in which a sample liquid is allowed to flow, a reservoir 30 in which the sample liquid is allowed to be stored, a liquid introduction inlet 40 for introducing the sample liquid into the microflow channel 20, a filter 50 for allowing passage of a fine particle in the sample liquid and an electrode 60 for providing the sample liquid with an electrical signal.

Specifically, the main surface of the semiconductor substrate 10 formed of, for example, Si is excavated to form the microflow channel 20 having a substrate-excavated shape. Insulating film 11 such as a silicon oxide film is formed on the bottom surface and side surfaces of the microflow channel 20 and the substrate 10. Further, insulating film 12 is formed on insulating film 11 in the portion except for the portion of the microflow channel 20. In the portion of the microflow channel 20, insulating film 12 is formed so as to have a hollow structure. A part of insulating film 12 is a cap layer which covers the upper part of the microflow channel 20.

The rectangular reservoir 30 is constructed at an end of the microflow channel 20 by forming a bank 14 on the substrate 10 in a go-around manner. In the reservoir 30, the liquid introduction inlet 40 is formed. The liquid introduction inlet 40 is connected to an end of the microflow channel 20. The liquid introduction inlet 40 is formed so as to be wider than the microflow channel 20. In other words, an end of the microflow channel 20 passes under the bank 14, is introduced into the reservoir 30 and is connected to the liquid introduction inlet 40 which is wider than the microflow channel 20.

In a manner similar to the microflow channel 20, the upper surface of the liquid introduction inlet 40 is covered by the cap layer 12. A plurality of micropores 13 are formed in the cap layer 12 to construct the filter 50. The shape of the micropores 13 of the filter 50 can be patterned in the cap layer 12 of the microflow channel 20 in a planar manner and can be freely designed.

The electrode 60 is formed in the area except for the area of the liquid introduction inlet 40 on insulating film 12 inside the bank 14. A part of the electrode 60 extends to outside of the reservoir 30 by passing between the bank 14 and insulating film 12.

A plurality of pillars may be formed in the microflow channel 20 in order to let the sample liquid more smoothly move in the microflow channel 20.

When a liquid such as a sample liquid is dropped in the reservoir 30 in the semiconductor microanalysis chip having the above structures, the dropped liquid spreads in the reservoir 30 and reaches the liquid introduction inlet 40. The liquid which has reached the liquid introduction inlet 40 goes through the filter 50, is introduced into the microflow channel 20 and flows into the block (not shown) which is connected to the microflow channel for analyzing liquid. At this time, the dropped liquid is blocked by the bank 14 forming the reservoir 30. Thus, it is possible to prevent the liquid from flowing to outside of the reservoir 30.

The electrode 60 formed in the reservoir 30 is capable of applying an electrical signal to the liquid dropped in the reservoir 30. It is possible to obtain the analysis result in the block (not shown) which is connected to the microflow channel 20 for analyzing liquid.

In addition, in the present embodiment, the filter 50 comprising the plurality of micropores 13 is provided in the liquid introduction inlet 40 between the reservoir 30 and the microflow channel 20. The size or shape of each micropore 13 is set such that a fine particle other than the inspection target is not allowed to pass through and the fine particle to be inspected is allowed to pass through each micropore 13. In this manner, only the fine particle to be inspected or the group of such fine particles is allowed to pass through the filter 50.

Figure 3B:
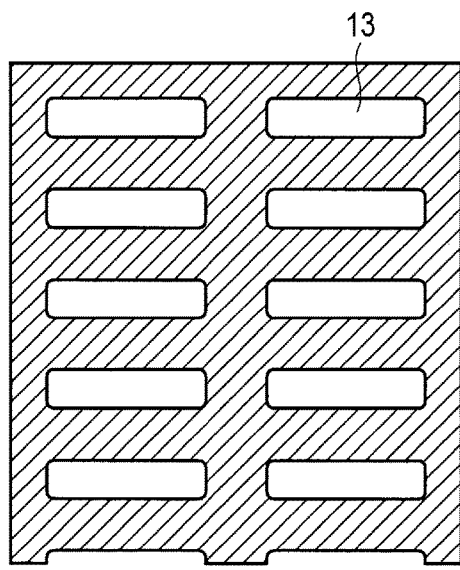
Figure 3C:
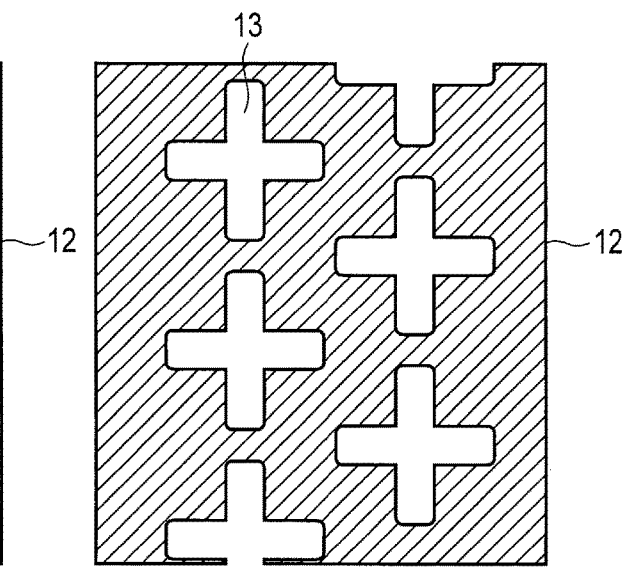

FIGS. 3A to 3C show pattern examples of the micropores 13 of the filter 50. In FIG. 3A, each micropore 13 is formed in a circular shape. In FIG. 3B, each micropore 13 is formed in a rectangular shape. In FIG. 3C, each micropore 13 is formed in a cross shape. In FIG. 3A, the radius of each micropore 13 is made so as to be larger than that of the fine particle to be inspected and smaller than that of a fine particle other than the inspection target. In this manner, fine particles other than the inspection target can be excluded. In FIG. 3B, fine particles other than the inspection target can be excluded by optimizing the combination of the long diameter and short diameter of each micropore 13. In FIG. 3C, the rectangles of FIG. 3B are combined. Thus, fine particles other than the inspection target can be excluded by optimizing the combination of the long diameter and short diameter.

If the radius of each micropore 13 for the filter 50 is made smaller than that of each micropore for fine particle detection, it is possible to prevent a fine particle other than the inspection target from being stuck in the micropore for fine particle detection. In this manner, inspection can be reliably performed. If the radius of each micropore 13 for the filter 50 is made larger than that of each micropore for fine particle detection, it is possible to immediately introduce a sample liquid into the microflow channel 20. In this manner, the inspection time can be shortened.

In the semiconductor microanalysis chip of the present embodiment, the filter 50 is formed in the reservoir 30. This structure enables fine particles other than the inspection target to be excluded from the liquid dropped in the reservoir 30 such as a sample liquid before introducing the liquid into the microflow channel 20. The filter 50 can be formed by providing the plurality of micropores 13 in the cap layer 12.

The present embodiment is similar to the conventional technique in terms of a flow channel structure formed by excavating the substrate. However, in the present embodiment, the filter can be formed on the flat surface. Thus, it is possible to easily increase the filter area and increase the filter cross-sectional area. While the excavating depth must be greater than or equal to the radius of the particle to be inspected, there is no need to further deeply excavate the substrate in connection with flow increase. Moreover, as the filter 50 can be formed by merely providing the micropores 13 in the planar cap layer 12, the flexibility of pattern of the micropores 13 is high. In this manner, fine particles other than the inspection target can be efficiently excluded.

The semiconductor microanalysis chip of the first embodiment is manufactured by the steps of the semiconductor process described below.

First, the excavating structure including the microflow channel 20 and the liquid introduction inlet 40 is formed on the silicon substrate 10 by using a reactive ion etching device. Subsequently, to prevent electrical conduction between the dropped liquid and the substrate 10, silicon oxide which is insulating film 11 is formed on the top surface of the substrate by thermal oxidation.

Next, the inner part of the microflow channel 20 and the liquid introduction inlet 40 is buried with a resinous material as a sacrificial layer (not shown). Insulating film (cap layer) 12 is formed by stacking silicon oxide on insulating film 11 and the sacrificial layer. After the formation of the cap layer 12, a Pt electrode is stacked on insulating film 12 by a lift-off process using a photoresist. Subsequently, the bank 14 is formed by application of epoxy resin and patterning. Further, to prevent the bank 14 from being etched in the next step for removing sacrificial layer, the surface of the epoxy resin is covered by silicon oxide. Lastly, the sacrificial layer in the microflow channel 20 is etched and removed by oxygen plasma asking.

At this time, the length of the short side of the liquid introduction inlet 40 in the perpendicular direction relative to the main surface of the substrate; that is, the width of the liquid introduction inlet 40 is made wider than the width of the microflow channel 20. This structure enables the liquid dropped in the reservoir 30 to efficiently reach the liquid introduction inlet 40 of the microflow channel 20. Further, the liquid introduction inlet 40 is covered by the cap layer 12 which covers the microflow channel 20. In this part, the micropores 13 are formed. In this manner, the filter 50 can be formed. By the filter 50, fine particles other than the inspection target can be excluded.

For the base material of the substrate 10, quartz, gallium arsenide, indium phosphide, sapphire, ceramic or fluoroplastic may be used as well as silicon. The process for excavating the substrate may be performed by using a method other than reactive ion etching. Insulating film 11 may be stacked on the main surface of the substrate 10 by using a method other than thermal oxidation, such as chemical vapor deposition or sputtering. Insulating film 11 may be unnecessary when the substrate 10 is an insulator.

For the material of the sacrificial layer, a semiconductor material such as silicon or gallium arsenide, a metal material such as aluminum or molybdenum, or an insulating material such as quartz or silicon nitride may be used as well as a resinous material. The sacrificial layer should be selected so as to be high in the etching selection ratio relative to the material of the cap layer stacked on the sacrificial layer.

The cap layer 12 is preferably formed of an insulating material such as silicon nitride, sapphire or resin as well as silicon oxide and should be selected so as to be high in the etching selection ratio relative to the sacrificial layer.

The material of the electrode 60 includes Pt, Ir, Pd, Au, Hg, Sn, Cu, Zn, Fe, Mg, Co, Ni, V, calomel and various combinations of these elements. Although an electro-chemical electrode such as Ag/AgCl or Hg/HgO may be used, a material which can be dealt with in a semiconductor process enabling mass production at low cost is preferably selected.

The electrode 60 may be patterned by an etching-off process such as dry etching or wet etching as well as a lift-off process.

For the material of the bank 14, a semiconductor material such as silicon or gallium arsenide, a metal material such as aluminum or molybdenum, or an insulating material such as quartz or silicon nitride may be used as well as a resinous material. For the material which covers the bank 14, an insulating material such as quartz or silicon nitride may be used as well as silicon oxide. If the material which covers the bank is not removed when the sacrificial layer of the microflow channel is etched and removed, there is no need to stack the cover. The size of the bank 14 should be appropriately set based on the volume of the liquid dropped in the reservoir 30.

The sacrificial layer may be etched by oxygen plasma ashing, dry etching using gas which enables removal of the sacrificial layer or wet etching using etchant. One of the above methods may be selected depending on the material of the sacrificial layer.

Now, this specification explains some problems of a semiconductor microanalysis chip comprising a reservoir formed by excavating a substrate as a comparison example.

Figure 15:
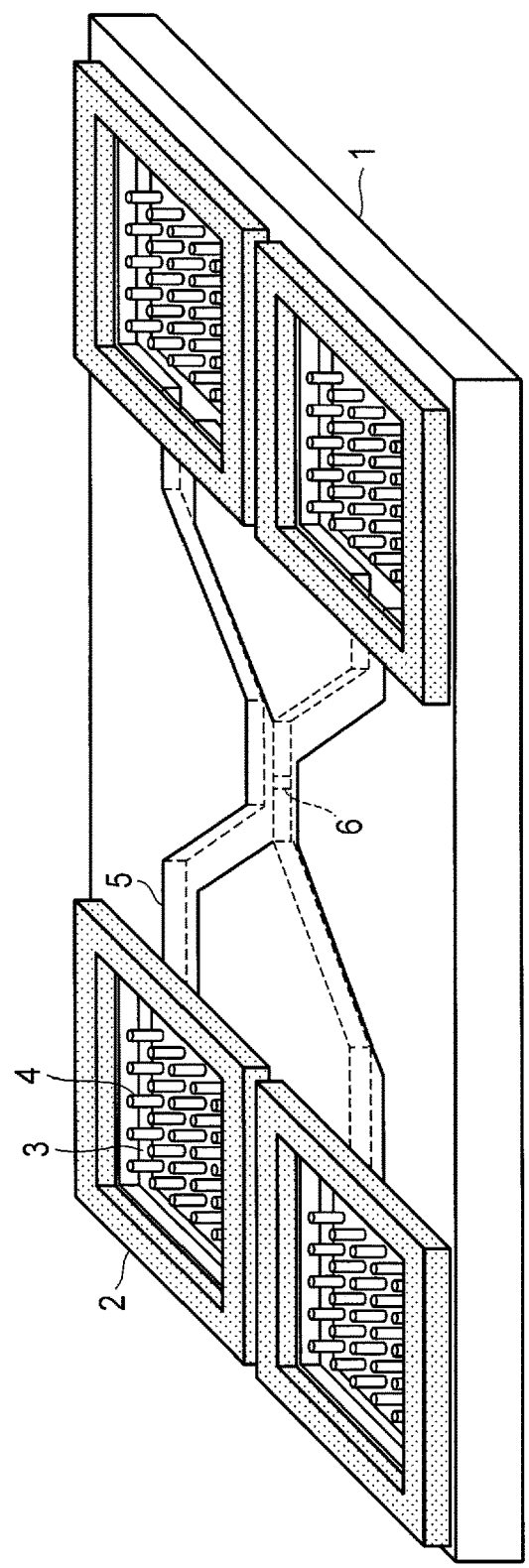
FIG. 15 is a perspective view showing the whole structure of a semiconductor microanalysis chip as a comparison example.

The semiconductor microanalysis chip of the comparison example comprises, as shown in FIG. 15, a bank 2 formed in a go-around manner on the main surface of a semiconductor substrate 1, a reservoir 3 formed by the bank 2, a pillar 4 formed by excavating a part of the main surface of the substrate, a microflow channel 5 similarly formed by excavating a part of the main surface of the substrate 1 and an electrode (not shown) formed in the reservoir 3. The upper part of the microflow channel 5 is covered by a cap layer. The microflow channel 5 extends from the inner side to outer side of the reservoir 3.

In a case of the reservoir 3 of this type of microanalysis chip, in which the pillar 4 is formed at the same time as excavating the substrate 1, the sample liquid dropped in the reservoir 3 can be introduced into the liquid introduction inlet of the microflow channel 5 formed by excavating the substrate 1 by capillarity of the pillar 4. The fine particles to be inspected in the introduced sample liquid are detected as change in electrical signals when the particles pass through a detection hole 6 of the microflow channel 5. However, since the effect of impurities such as fine particles other than the inspection target is a concern, it is necessary to remove such impurities by a filter between the reservoir 2 and the detection hole.

In the structure of the comparison example, the filter is formed by the pillar 4. The filter formed by the pillar 4 has some problems. In the flow channel structure formed by excavating the substrate 1, it is necessary to increase the cross-sectional area of the flow channel in accordance with increase in the flow volume of the sample liquid passing through the flow channel and increase in the particle radius of the inspection target. To increase the cross-sectional area of the flow channel, the excavating depth of the substrate needs to be increased. Thus, the pillar shape has a high-aspect-ratio. The comparison example causes a structural problem in which many breaking troubles of the pillar occur at the time of processing the pillar and the subsequent steps.

In a case of the filter using the pillar, the shape of the pillar is limited to a column shape. Therefore, the shape of a through-hole of the filter is limited to a rectangular parallelepiped shape, etc.

For example, a circular shape or a cross shape is impossible. Thus, this example also entails a designing problem. Moreover, in the flow channel structure formed by excavating the substrate, the excavating depth is limited. This causes a performance problem in which the filter area cannot be increased.

In the present embodiment, the filter 50 can be constructed by providing the micropores 13 in the cap layer 12 formed on the planar surface. In this manner, the present embodiment is stable in terms of the structure and has improved flexibility in terms of designing.

Second Embodiment

Figure 4:
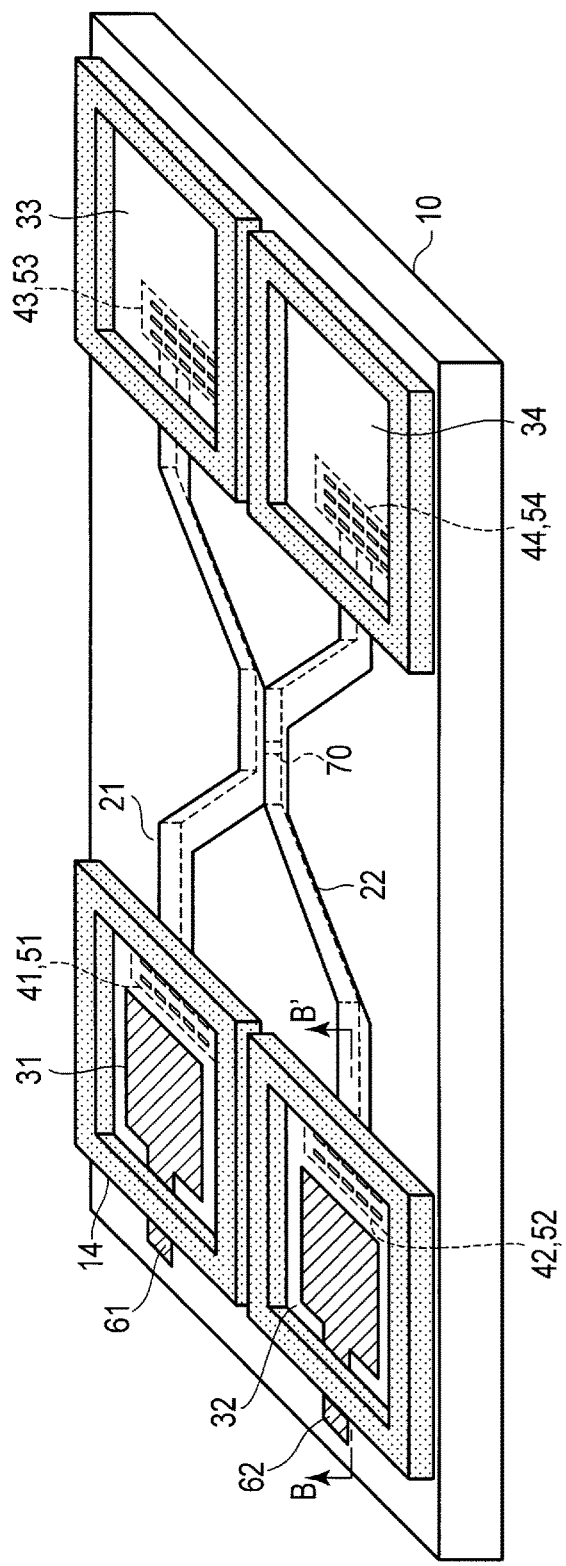
FIG. 4 is a planar view showing the whole structure of a semiconductor microanalysis chip according to a second embodiment.

FIG. 4 is a planar view showing the whole structure of a semiconductor microanalysis chip according to a second embodiment. The elements identical to those of FIG. 1 are denoted by the same reference numbers as FIG. 1. Thus, the detailed explanation of such elements is omitted. FIG. 2 also corresponds to the cross-sectional surface taken along the arrow B-B' of FIG. 4.

The present embodiment is an example in which the structure of the reservoir explained in the first embodiment is applied to a semiconductor microanalysis chip comprising two microflow channels.

As shown in FIG. 4, the semiconductor microanalysis chip of the present embodiment comprises a semiconductor substrate 10, first to fourth reservoirs 31 to 34, liquid introduction inlets 41 to 44, filters 51 to 54, first and second microflow channels 21 and 22, first and second electrodes 61 and 62 formed in the first and second reservoirs 31 and 32 and a micro slit 70 for fine particle detection. In a manner similar to the first embodiment, an insulating film is formed at least on the main surface of the substrate, and further, a cap layer which covers the top surfaces of the microflow channels 21 and 22 is formed (not shown).

Specifically, a part of the main surface of the substrate 10 is excavated to form the first and second microflow channels 21 and 22 having a substrate-excavating shape. The microflow channels 21 and 22 are partially adjacent to each other. The micro slit 70 for fine particle detection is provided in the partition wall of the adjacent portion.

At an end of the first microflow channel 21, the first reservoir 31 is constructed by forming a bank 14 on the substrate in a go-around manner. An end of the first microflow channel 21 leads to inside of the first reservoir 31 and has a wide width. The first microflow channel 21 comprises liquid introduction inlet 41 in the first reservoir 31. Filter 51 is formed in liquid introduction inlet 41. Filter 51 comprises a cap layer in which a micropore is provided. The first electrode 61 is formed on the top surface of the substrate 10 in the first reservoir 31. A part of the electrode 61 extends to outside of the reservoir 31 through the bottom portion of the bank 14.

At an end of the second microflow channel 22, the second reservoir 32 is constructed by forming the bank 14 on the substrate 10 in a go-around manner. The second reservoir 32 substantially has the same structure as the first reservoir 31 and comprises liquid introduction inlet 42, filter 52 and the second electrode 62. Liquid introduction inlet 42 is connected to the second microflow channel 22.

At the other end of the first microflow channel 21, the third reservoir 33 is constructed by forming the bank 14 on the substrate 10 in a go-around manner. The structure of the third reservoir 33 is the same as that of the first reservoir 31 except that the third reservoir 33 does not comprise the first electrode 61. At the other end of the second microflow channel 22, the fourth reservoir 34 is constructed by forming the bank 14 on the substrate in a go-around manner. The structure of the fourth reservoir 34 is the same as that of the second reservoir 32 except that the fourth reservoir 34 does not comprise the second electrode 62.

As described above, the first microflow channel 21 connects liquid introduction inlet 41 in the first reservoir 31 and liquid introduction inlet 43 in the third reservoir 33. The upper surface of the first microflow channel 21 is covered by a cap layer. The second microflow channel 22 connects liquid introduction inlet 42 in the second reservoir 32 and liquid introduction inlet 44 in the fourth reservoir 34. The upper surface of the second microflow channel 22 is covered by a cap layer.

If a sample liquid flows in only one direction from the first reservoir 31 to the third reservoir 33, filter 53 in the third reservoir 33 may be omitted. If a sample liquid flows in only one direction from the second reservoir 32 to the fourth reservoir 34, filter 54 in the fourth reservoir 34 may be omitted.

When a liquid such as a sample liquid is dropped in the first reservoir 31 of the semiconductor microanalysis chip having the above structures, in a manner similar to the first embodiment, the dropped liquid spreads in the reservoir 31 and reaches liquid introduction inlet 41. The liquid which has reached liquid introduction inlet 41 is introduced into the first microflow channel 21 through filter 51. The liquid introduced into the first microflow channel 21 further passes through filter 53 in the third reservoir 33 and reaches the third reservoir 33.

When a liquid such as a sample liquid is dropped in the second reservoir 32, the dropped liquid spreads in the second reservoir 32 and reaches liquid introduction inlet 42. The liquid which has reached liquid introduction inlet 42 is introduced into the second microflow channel 22 through filter 52. The liquid introduced into the second microflow channel 22 further passes through filter 54 in the fourth reservoir 34 and reaches the fourth reservoir 34 via filter 54.

At this time, the liquid in the first microflow channel 21 is electrically connected with the first electrode 61 via liquid introduction inlet 41 and filter 51 in the first reservoir 31. In a similar manner, the liquid in the second microflow channel 22 is electrically connected with the second electrode 62 via liquid introduction inlet 42 and filter 52 in the second reservoir 32. Moreover, the liquid in the first microflow channel 21 contacts the liquid in the second microflow channel 22 via the micro slit 70. Thus, the first electrode 61 and the second electrode 62 are electrically connected with each other through the dropped liquid.

When voltage is applied between the first electrode 61 and the second electrode 62 in a state where a conductive sample liquid containing the substance to be inspected such as a fine particle is dropped in the first reservoir 31 and the second reservoir 32, an ionic current flows between the electrodes 61 and 62. In other words, an ionic current flows in accordance with the electrical conductivity of the sample liquid, the size and material of the first and second electrodes 61 and 62, the size of the first and second microflow channels 21 and 22 and the size of the micro slit 70, etc. An electric field is generated in the first and second microflow channels 21 and 22 and the micro slit 70 in accordance with the current density of the ionic current. In particular, the electric field intensity is the greatest near the micro slit 70 which is smaller than the first microflow channel 21 or the second microflow channel 22 in size. As the surface of the substance to be inspected in the sample liquid such as a fine particle normally takes charge, electrophoresis is caused by the surface charge and the aforementioned electric field.

The move by the electrophoresis of fine particles is vigorous near the micro slit 70 having high electric field intensity. In some cases, fine particles move from the first microflow channel 21 to the second microflow channel 22 via the micro slit 70 or move in the opposite direction. At this time, the sample liquid of the micro slit 70 is excluded by fine particles. In this manner, the electrical resistance of the micro slit 70 increases. As a result, the ionic current decreases.

The change amount and time of ionic current correspond to the size of fine particles which pass through the micro slit 70. Therefore, it is possible to electrically analyze the size of fine particles in the sample liquid by measuring the ionic current which flows between the first electrode 61 and the second electrode 62.

In the first microflow channel 21 and the second microflow channel 22, filter 50 (51, 52) explained in the first embodiment is formed. This structure enables fine particles other than the inspection target in the sample liquid to be excluded in advance. In this manner, it is possible to efficiently detect fine particles by using the micro slit 70.

When fine particles move via the micro slit 70 in only one direction from the first flow channel 21 to the second flow channel 22, a sample liquid does not always have to be introduced into the second flow channel 22. For example, an electrolyte solution which enables electrical detection between the electrodes 61 and 62 may be introduced.

Third Embodiment

Figure 6A:
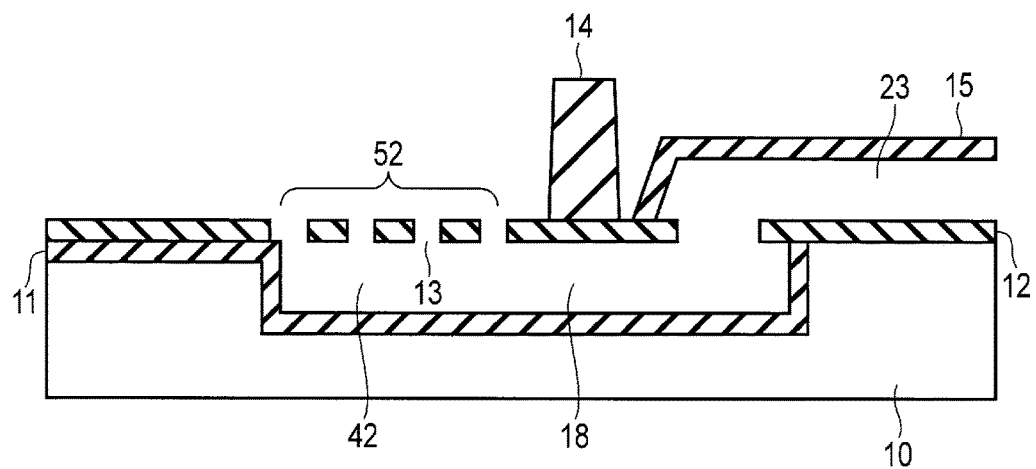
FIGS. 6A and 6B are cross-sectional views taken along the arrow C-C' of FIG. 5.
Figure 6B:
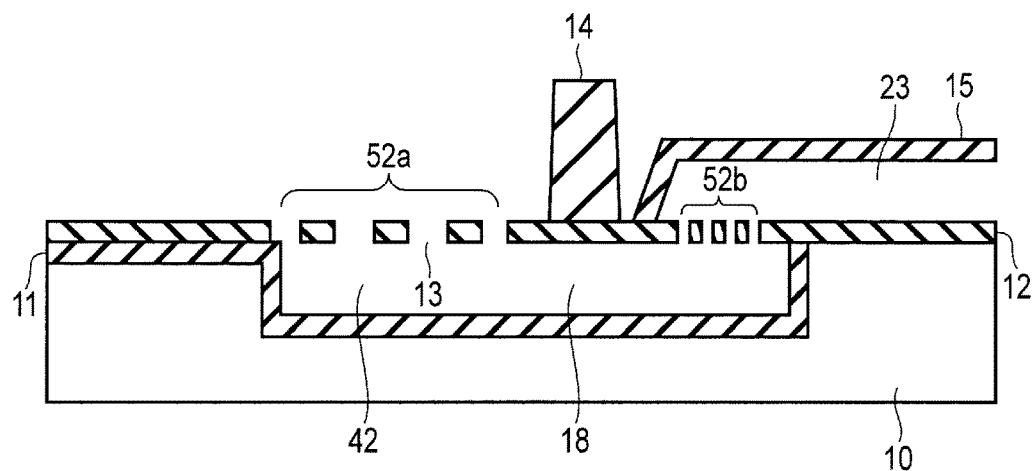

FIG. 5 is a planar view showing the whole structure of a semiconductor microanalysis chip according to a third embodiment. FIG. 6A and FIG. 6B are cross-sectional views taken along the arrow C-C' of FIG. 5. The elements identical to those of FIG. 2 and FIG. 4 are denoted by the same reference numbers as FIG. 2 and FIG. 4. Thus, the detailed explanation of such elements is omitted. Electrode 61 or 62 is not shown.

The present embodiment is different from the second embodiment explained above in respect that one of the microflow channels is formed in the shape of an insulating film tunnel.

A first microflow channel 21 has a substrate-excavating shape like the second embodiment. A second microflow channel 23 does not have a substrate-excavating shape and has an insulating film tunnel shape in which a hollow structure is formed of an insulating film on a substrate 10. The second microflow channel 23 is not formed inside the substrate 10 and is formed on the substrate 10. Thus, the second microflow channel 23 is positioned above the first microflow channel 21. The second microflow channel 23 intersects with the first microflow channel 21 in the central portion of the substrate 10. In the intersection, a micropore 80 for detection is formed.

To construct the second microflow channel 23, an insulating film 15 is formed so as to cover a sacrificial layer after the pattern of the sacrificial layer is formed on the substrate 10. Subsequently, the sacrificial layer is removed, thereby forming a flow channel having the shape of an insulating film tunnel. As shown in FIG. 6A, the second microflow channel 23 is connected to liquid introduction inlet 42 in a second reservoir 32 via a connecting passage 18 formed by excavating the substrate 10. Filter 52 is formed in liquid introduction inlet 42.

In the structure of the present embodiment, in a manner similar to the second embodiment, when a liquid such as a sample liquid is dropped in a first reservoir 31, the dropped liquid reaches introduction inlet 41 and is introduced into the first microflow channel 21 through filter 51. The liquid further passes through filter 52 and reaches a third reservoir 33. When a liquid such as a sample liquid is dropped in the second reservoir 32, the dropped liquid spreads in the second reservoir 32 and reaches liquid introduction inlet 42. The liquid which has reached liquid introduction inlet 42 is introduced into the connecting passage 18 through filter 52. The liquid is further introduced into the second microflow channel 23. The liquid introduced into the second microflow channel 23 reaches a fourth reservoir 34 through filter 54 in the fourth reservoir 34. Thus, fine particles can be inspected in a manner similar to the second embodiment.

In the present embodiment, an effect similar to that of the second embodiment can be obtained. In addition, in the present embodiment, the micropore 80 for fine particle inspection can be formed in a cap layer 12 in a planar manner. Thus, the designing flexibility of the hole shape is high. It is possible to optimally set the micropore 80 in accordance with the shape of the fine particles to be detected and improve the inspection accuracy.

In the present embodiment, a filter may be provided in the portion connecting the connecting passage 18 and the flow channel 23 in the structure shown in FIG. 6A. If, as shown in FIG. 6B, filter 52a of the liquid introduction inlet is made coarse and filter 52b on the connection side is made fine, it is possible to further efficiently exclude fine particles other than the inspection target.

Fourth Embodiment

Figure 7:
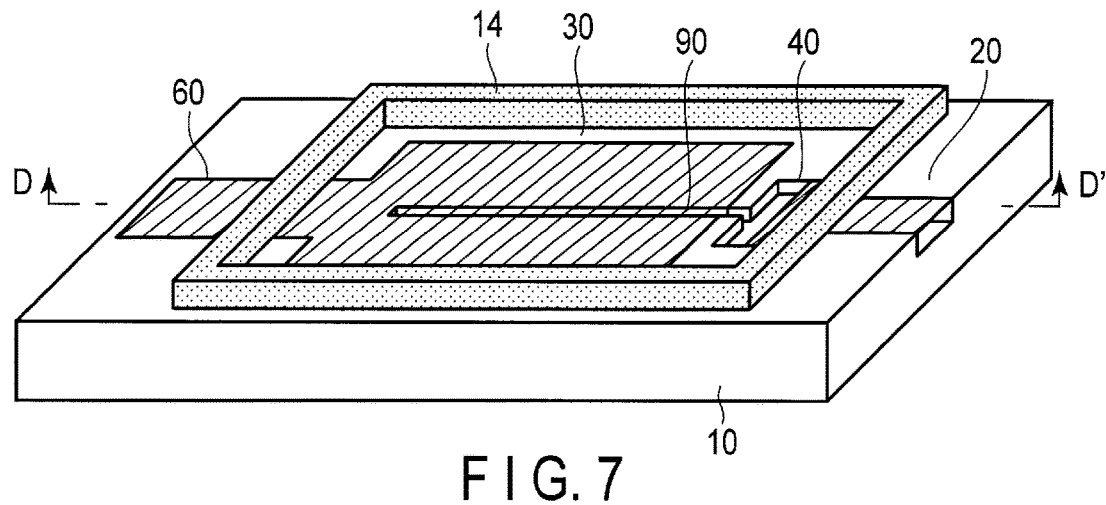
FIG. 7 is a perspective view showing the main structure of a semiconductor microanalysis chip according to a fourth embodiment.
Figure 8:
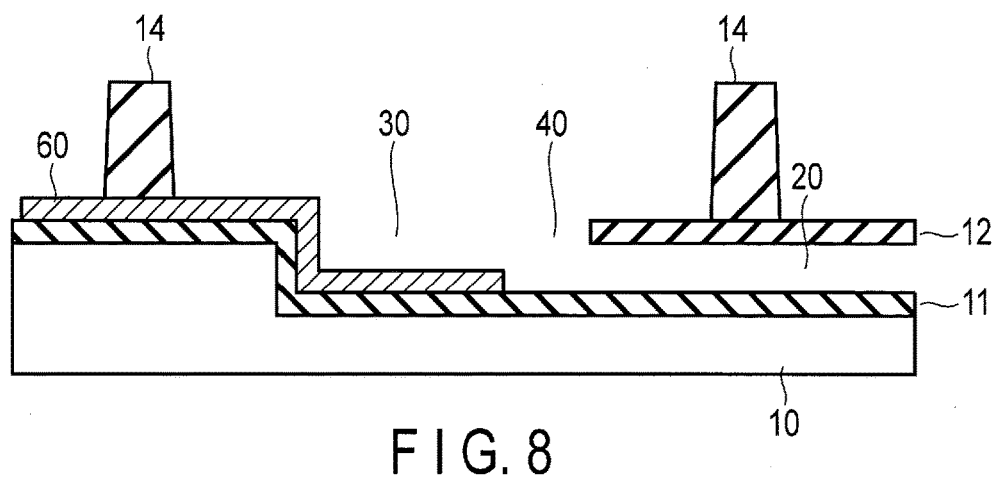
FIG. 8 is a cross-sectional view taken along the arrow D-D' of FIG. 7.

FIG. 7 and FIG. 8 are shown for explaining the outline structure of a semiconductor microanalysis chip according to a fourth embodiment. FIG. 7 is a perspective view showing the structure of a reservoir portion. FIG. 8 is a cross-sectional view taken along the arrow D-D' of FIG. 7. The elements identical to those of FIG. 1 and FIG. 2 are denoted by the same reference numbers as FIG. 1 and FIG. 2. Thus, the detailed explanation of such elements is omitted.

The semiconductor microanalysis chip of the present embodiment comprises a semiconductor substrate 10, a microflow channel 20 in which a sample liquid is allowed to flow, a reservoir 30 in which the sample liquid is allowed to be stored, a liquid introduction inlet 40 for introducing the sample liquid into the microflow channel 20, an electrode 60 for providing the sample liquid with an electrical signal and a liquid introduction structure 90 for leading the sample liquid to the liquid introduction inlet 40.

Specifically, the microflow channel 20 having a substrate-excavating shape is constructed by excavating the main surface of the semiconductor substrate 10 formed of, for example, Si. Insulating film 11 such as a silicon oxide film is formed on the bottom surface and side surfaces of the microflow channel 20 and the substrate 10. In the portion other than the portion of the microflow channel 20, insulating film 12 is formed on insulating film 11. Insulating film 12 is provided so as to form a hollow structure in the portion of the microflow channel 20. A part of insulating film 12 is a cap layer which covers the upper part of the microflow channel 20.

At an end of the microflow channel 20, the rectangular reservoir 30 is constructed by forming a bank 14 on the substrate 10 in a go-around manner. In the reservoir 30, the liquid introduction inlet 40 is formed. The liquid introduction inlet 40 is connected to an end of the microflow channel 20. The liquid introduction inlet 40 is wider than the microflow channel 20. An end of the microflow channel 20 leads to the reservoir 30 by passing under the bank 14 and is connected to the liquid introduction inlet 40 which is wider than the microflow channel 20.

The liquid introduction structure 90 is formed in the reservoir 30. The liquid introduction structure 90 comprises a groove formed by linearly excavating the substrate 10. Here, the liquid introduction structure 90 comprises a linear groove. An end of the liquid introduction structure 90 is connected to the liquid introduction inlet 40.

The electrode 60 is formed on insulating film 11 in the reservoir 30. A part of the electrode 60 extends to outside of the reservoir 30 by passing between the bank 14 and insulating film 11. The electrode 60 may be formed in the liquid introduction structure 90 and may be formed in an area other than the area of the liquid introduction structure 90.

When a liquid such as a sample liquid is dropped in the reservoir 30 of the semiconductor microanalysis chip having the above structures, the dropped liquid spreads in the reservoir 30, is captured by the liquid introduction structure 90 and reaches the liquid introduction inlet 40. The liquid which has reached the liquid introduction inlet 40 is introduced into the microflow channel 20 and moves to the block (not shown) which is connected to the microflow channel 20 for analyzing liquid. If the liquid introduction structure 90 is made several to several hundreds micrometers wide, the liquid captured by the liquid introduction structure 90 can immediately reach the liquid introduction inlet 40 by capillarity. Moreover, since the current speed in the liquid introduction structure 90 is higher than the current speed in the microflow channel 20, the sample liquid can be continuously introduced into the microflow channel 20. Further, the dropped liquid is blocked by the bank 14 forming the reservoir 30. Thus, it is possible to prevent the liquid from flowing into outside of the reservoir 30.

The electrode 60 formed on insulating film 11 in the reservoir 30 is capable of applying an electrical signal to the liquid dropped in the reservoir 30. It is possible to obtain, through the dropped liquid, the analysis result in the block (not shown) which is connected to the microflow channel 20 for analyzing liquid. At this time, a large part of the electrode 60 is stacked on insulating film 11 excluding the liquid introduction structure 90. In other words, a large part of the electrode 60 is stacked on the flat insulating film 11 positioned on the main surface of the substrate 10. Thus, it is possible to prevent many problems including the restriction in electrode layout and the electrode disconnection caused by electrode formation on an insulating film side surface.

The semiconductor microanalysis chip of the fourth embodiment is manufactured by the steps of the semiconductor process described below.

First, an excavating structure including the liquid introduction structure 90 and the microflow channel 20 is formed on the silicon substrate 10 by using a reactive ion etching device. Subsequently, to prevent electrical conduction between the dropped liquid and the substrate 10, silicon oxide which is insulating film 11 is formed on the top surface of the substrate by thermal oxidation.

Next, the inner part of the microflow channel 20 is buried by a resinous material as a sacrificial layer (not shown). Silicon oxide is stacked on the resinous material, thereby forming the cap layer 12. After the formation of the cap layer 12, a Pt electrode is formed on insulating film 11 by a lift-off process using a photoresist. Moreover, the bank 14 is formed by patterning epoxy resin. To prevent the bank 14 from being etched in the next step for removing the sacrificial layer, the top surface of the epoxy resin is covered by silicon oxide. Lastly, the sacrificial layer in the microflow channel 20 is etched and removed by oxygen plasma ashing.

The excavating structures of the liquid introduction structure 90 and the microflow channel 20 may be formed either simultaneously or separately. When the structures are formed simultaneously, it is possible to decrease the number of steps of the process for manufacturing the semiconductor microanalysis chip. Thus, the production cost can be reduced. In this case, the excavating amount of the liquid introduction structure 90 is substantially the same as that of the microflow channel 20.

The length of the short side of the liquid introduction structure 90 in the perpendicular direction relative to the main surface of the substrate; that is, the width of the liquid introduction structure 90 is made narrower than the width of the microflow channel 20. In this structure, the capillary force is increased. Thus, the liquid dropped in the reservoir 30 can reach the liquid introduction inlet 40 of the microflow channel 20 in a short time. Moreover, a part of the liquid introduction structure 90 is covered by the cap layer 12 which covers the microflow channel 20. This structure enables the dropped liquid to be introduced into the liquid introduction structure 90 only from a specific area. Thus, foreign substances in the liquid can be filtered.

In the present embodiment, the liquid introduction structure 90 is formed in the reservoir 30. In this structure, the liquid dropped in the reservoir 30 such as a sample liquid can be immediately guided to the liquid introduction inlet 40 of the of the microflow channel 20, and further, the liquid can be introduced into the microflow channel 20. At this time, for example, the process for excavating a large part of the inner portion of the reservoir 30 to form a pillar is unnecessary. The electrode 60 is formed on the flat insulating film 11 positioned on the main surface of the substrate. In this manner, dragging of the electrode 60 can be avoided, and restriction on the electrode size can be relaxed.

It is possible to solve both the problem of a microanalysis chip comprising a reservoir formed by an excavating process and the problem of a microanalysis chip comprising a reservoir formed without an excavating process. In other words, the present embodiment can realize a semiconductor microanalysis chip which can immediately introduce a sample liquid into the microflow channel 20, prevent the disconnection defect of the electrode 60 and relax restrictions on the electrode area while restraining the production cost.

For the materials of the substrate 10, insulating film 11, the cap layer 12, the electrode 60, the bank 14 and the sacrificial layer, various materials explained in the first embodiment can be used. Further, with respect to the patterning of the electrode 60 and the etching of the sacrificial layer, various modifications explained in the first embodiment can be applied.

In the semiconductor analysis chip of the present embodiment, the electrode 60 is stacked on the bottom surface and side surfaces of the liquid introduction structure 90. However, when the electrode on the bottom surface and the side surfaces is disconnected with the electrode in the other portions, or electrode lamination on these areas is difficult, the electrode 60 may be formed only on insulating film 11 on the main surface of the substrate other than the liquid introduction structure 90.

In preparation for a case where a sample liquid is introduced into the liquid introduction inlet 40 without passing through the liquid introduction structure 90, in a manner similar to the first embodiment, a filter may be formed by covering the top surface of the liquid introduction inlet 40 with a cap layer like the microflow channel and providing a micropore in the cap layer.

Fifth Embodiment

Figure 9:
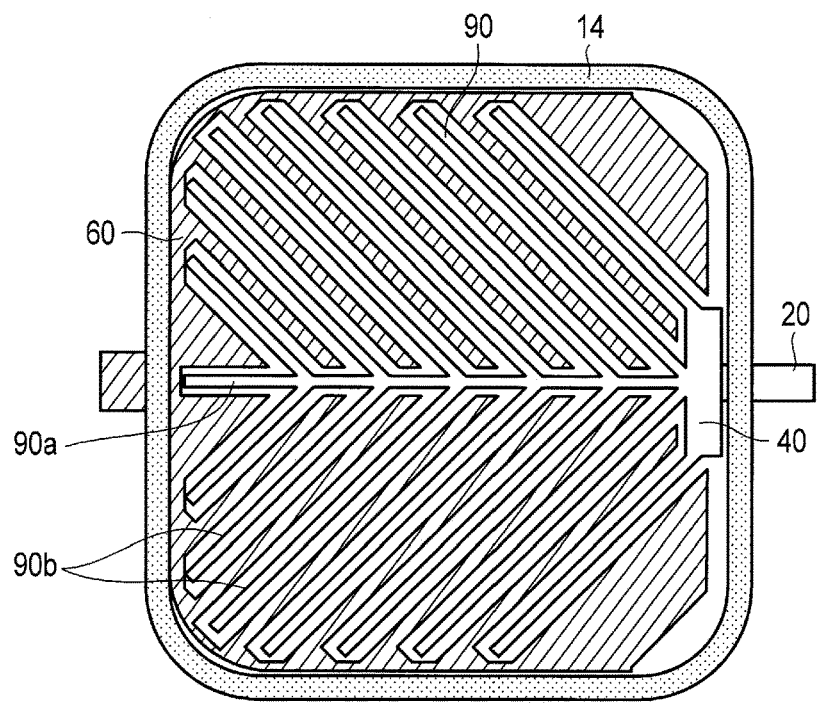
FIG. 9 is a planar view showing the main structure of a semiconductor microanalysis chip according to a fifth embodiment.

FIG. 9 is a planar view showing the main structure of a semiconductor microanalysis chip according to a fifth embodiment. The elements identical to those of FIG. 7 are denoted by the same reference numbers as FIG. 7. Thus, the detailed explanation of such elements is omitted.

As shown in FIG. 9, the present embodiment is the same as the fourth embodiment except for liquid introduction structure 90. Liquid introduction structure 90 (90a, 90b) of the present embodiment is a linear groove. A plurality of liquid introduction structures (90a) are connected to a liquid introduction inlet 40. A plurality of liquid introduction structures (90b) are connected to liquid introduction structure 90a in midstream. Here, liquid introduction structure 90 is a linear groove. Liquid introduction structure 90 is formed in the shape of arrow feather.

By dropping a liquid such as a sample liquid in the above structure, the liquid captured by liquid introduction structure 90 ultimately reaches the liquid introduction inlet 40 while binding with liquid introduction structure 90 in midstream in a manner similar to the fourth embodiment. Liquid introduction structure 90 is allocated in many places of a reservoir 30. Thus, the dropped sample liquid reaches liquid introduction structure 90 and is introduced into a microflow channel 20 via the liquid introduction inlet 40 in a shorter time than the fourth embodiment. Moreover, compared to the fourth embodiment, the flexibility of the place in which a sample liquid is dropped is increased.

The method for manufacturing the semiconductor microanalysis chip of the present embodiment is the same as that of the process explained in the fourth embodiment except that the pattern of liquid introduction structure 90 is different between the embodiments.

Sixth Embodiment

Figure 10:
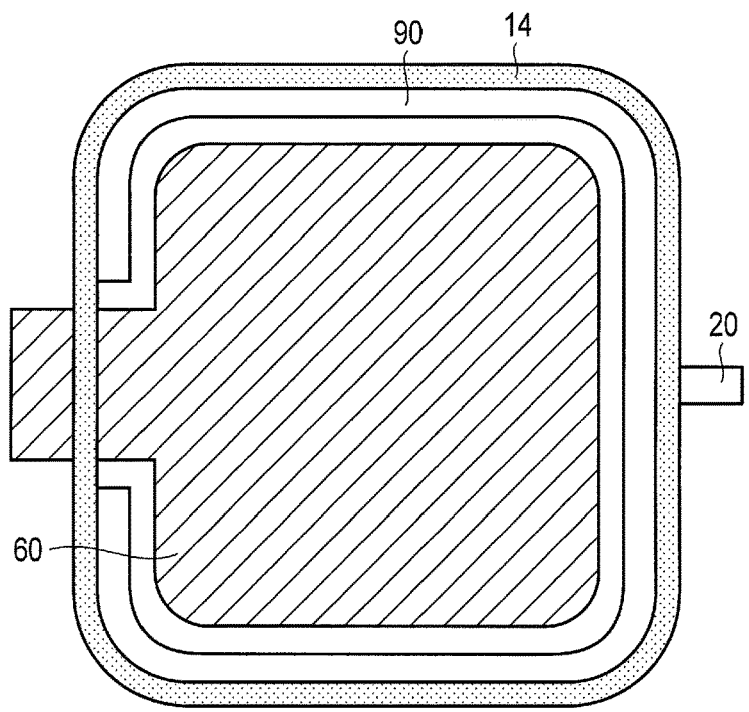
FIG. 10 is a planar view showing the main structure of a semiconductor microanalysis chip according to a sixth embodiment.

FIG. 10 is a planar view showing the main structure of a semiconductor microanalysis chip according to a sixth embodiment. The elements identical to those of FIG. 7 are denoted by the same reference numbers as FIG. 7. Thus, the detailed explanation of such elements is omitted.

As shown in FIG. 10, the present embodiment has the same structure as the fourth embodiment except for a liquid introduction structure 90. The liquid introduction structure 90 of the present embodiment is formed along the vicinity of the inner wall of a bank 14 substantially in a concentric manner with respect to a reservoir 30. In short, the liquid introduction structure 90 comprises a linear and curved groove.

Of the liquid dropped in the reservoir 30, the liquid which contacts the bank 14 spreads around the bank 14 by capillarity faster than spreading inside the reservoir 30. Thus, the structure of the present embodiment enables the liquid around the bank 14 to be captured in the liquid introduction structure 90. As a result, the liquid dropped in the reservoir 30 can be introduced into a microflow channel 20 via a liquid introduction inlet 40 in a shorter time than the semiconductor microanalysis chip of the fourth embodiment. Moreover, the place in which the sample liquid is dropped can be the inner wall of the bank 14. Thus, for example, it is possible to place a jig for introducing the sample liquid based on the support of the bank 14.

The method for manufacturing the semiconductor microanalysis chip of the present embodiment is the same as that of the fourth embodiment except that the pattern of the liquid introduction structure 90 is different between the embodiments. It is possible to form a liquid introduction structure by combining the liquid introduction structure of the semiconductor microanalysis chip of the fifth embodiment.

Seventh Embodiment

Figure 11:
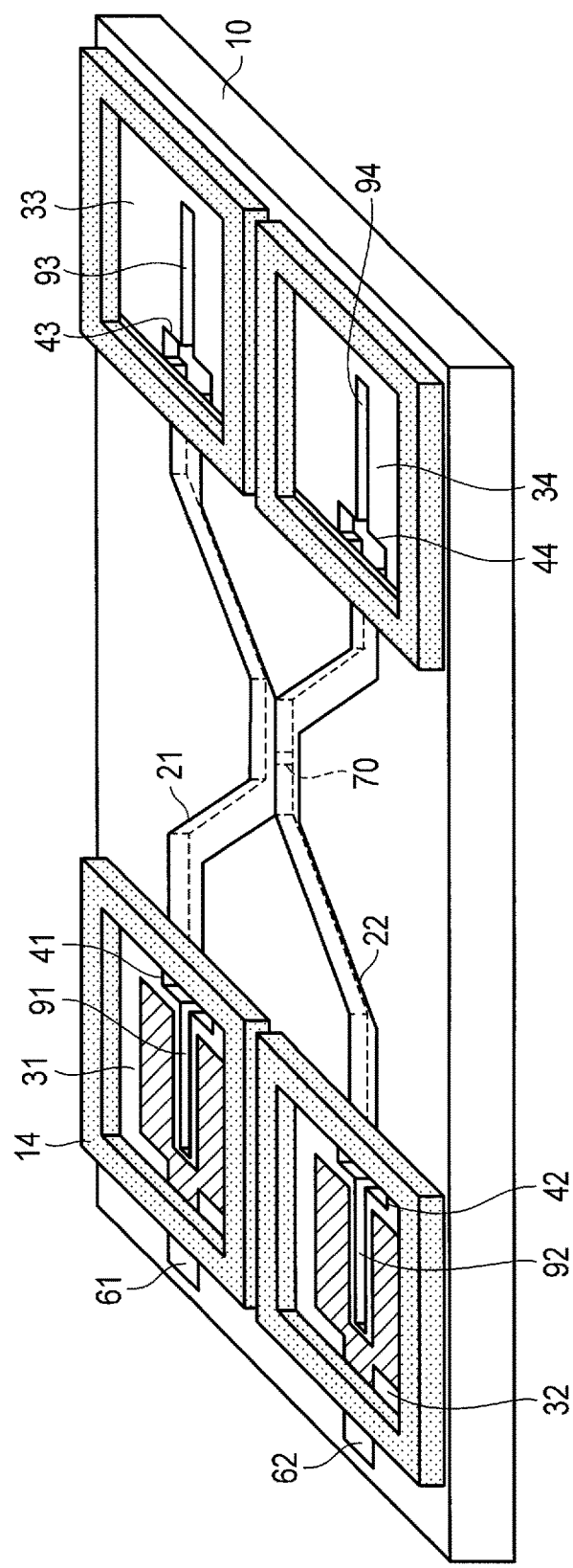
FIG. 11 is a perspective view showing the whole structure of a semiconductor microanalysis chip according to a seventh embodiment.

FIG. 11 is a perspective view showing the whole structure of a semiconductor microanalysis chip according to a seventh embodiment. The elements identical to those of FIG. 7 are denoted by the same reference numbers as FIG. 7. Thus, the detailed explanation of such elements is omitted.

The present embodiment is an example in which the structure of the reservoir explained in the fourth embodiment is applied to a semiconductor microanalysis chip comprising two microflow channels.

As shown in FIG. 11, the semiconductor microanalysis chip of the present embodiment comprises a semiconductor substrate 10, first to fourth reservoirs 31 to 34, liquid introduction structures 91 to 94, liquid introduction inlets 41 to 44, first and second microflow channels 21 and 22, first and second electrodes 61 and 62 formed in the first and second reservoirs 31 and 32 and a micro slit 70 for fine particle detection. In a manner similar to the first embodiment, an insulating film is formed at least on the main surface of the substrate, and further, a cap layer is formed so as to cover the top surfaces of the microflow channels 21 and 22 (not shown).

Specifically, the first and second microflow channels 21 and 22 having a substrate-excavating shape are formed by excavating a part of the main surface of the substrate 10. The microflow channels 21 and 22 are partially adjacent to each other. The micro slit 70 for fine particle detection is provided in the partition wall of the adjacent portion.

At an end of the first microflow channel 21, the first reservoir 31 is constructed by forming a bank 14 on the substrate in a go-around manner. In the reservoir 31, liquid introduction structure 91 is formed by linearly excavating the top surface of the substrate 10.

An end of the first microflow channel 21 leads to inside of the first reservoir 31 and has a wide width. The first microflow channel 21 comprises liquid introduction inlet 41 in the first reservoir 31. Liquid introduction structure 91 is connected to liquid introduction inlet 41. The first electrode 61 is formed on the top surface of the substrate 10 in the first reservoir 31. A part of the electrode 61 extends to outside of the reservoir 31 through the bottom portion of the bank 14.

At an end of the second microflow channel 22, the second reservoir 32 is constructed by forming the bank 14 on the substrate in a go-around manner. The second reservoir 32 substantially has the same structure as the first reservoir 31 and comprises liquid introduction inlet 42, the second electrode 62 and liquid introduction structure 92. Liquid introduction inlet 42 is connected to the second microflow channel 22.

At the other end of the first microflow channel 21, the third reservoir 33 is constructed by forming the bank 14 on the substrate in a go-around manner. The structure of the third reservoir 33 is the same as that of the first reservoir 31 except that the third reservoir 33 does not comprise the first electrode 61. The structure of member 43 is the same as that of member 41. The structure of member 93 is the same as that of member 91. When liquid moves from the reservoir 31 to the reservoir 33, member 43 functions as a liquid outlet, and member 93 functions as a liquid discharging structure.

At the other end of the second microflow channel 22, the fourth reservoir 34 is constructed by forming the bank 14 on the substrate in a go-around manner. The structure of the fourth reservoir 34 is the same as that of the second reservoir 32 except that the fourth reservoir 34 does not comprise the second electrode 62. Here, in a manner similar to the case of the third reservoir 33, member 44 functions as a liquid outlet, and member 94 functions as a liquid discharging structure. Since an electrode is unnecessary on the liquid discharging side, a plurality of pillars may be provided instead of providing the liquid discharging structures 93 and 94.

As explained above, the first microflow channel 21 connects liquid introduction inlet 41 in the first reservoir 31 and liquid introduction inlet 43 in the third reservoir 33. The upper surface of the first microflow channel 21 is covered by a cap layer. The second microflow channel 22 connects liquid introduction inlet 42 in the second reservoir 32 and liquid introduction inlet 44 in the fourth reservoir 34. The upper surface of the second microflow channel 22 is covered by a cap layer.

When a liquid such as a sample liquid is dropped in the first reservoir 31 of the semiconductor microanalysis chip having the above structures, in a manner similar to the first embodiment, the dropped liquid spreads in the first reservoir 31, is captured by liquid introduction structure 91 and reaches liquid introduction inlet 41. The liquid which has reached liquid introduction inlet 41 is immediately introduced into the first microflow channel 21. The liquid introduced into the first microflow channel 21 immediately reaches liquid introduction structure 93 via liquid introduction inlet 43 in the third reservoir 33.

When a liquid such as a sample liquid is dropped in the second reservoir 32, the dropped liquid spreads in the second reservoir 32, is captured by liquid introduction structure 92 and reaches liquid introduction inlet 42. The liquid which has reached liquid introduction inlet 42 is immediately introduced into the second microflow channel 22. Further, the liquid introduced into the second microflow channel 22 immediately reaches liquid introduction structure 94 via liquid introduction inlet 44 in the fourth reservoir 34.

The liquid in the first microflow channel 21 is electrically connected with the first electrode 61 via liquid introduction structure 91 and liquid introduction inlet 41 in the first reservoir 31. In a similar manner, the liquid in the second microflow channel 22 is electrically connected with the second electrode 62 via liquid introduction structure 92 and liquid introduction inlet 42 in the second reservoir 32. Further, the liquid in the first microflow channel 21 contacts the liquid in the second microflow channel 22 via the micro slit 70. In this manner, the first electrode 61 and the second electrode 62 are electrically connected with each other through the dropped liquid.

When voltage is applied between the first electrode 61 and the second electrode 62 in a state where a conductive sample liquid containing the substance to be inspected such as a fine particle is dropped in the first reservoir 31 and the second reservoir 32, an ionic current flows between the electrodes 61 and 62 in a manner similar to the second embodiment explained above. An electric field is generated in the first and second microflow channels 21 and 22 and the micro slit 70 in accordance with the current density of the ionic current. The substance to be inspected in the sample liquid such as a fine particle is electrophoresed by the aforementioned electric field. Thus, in a manner similar to the second embodiment, the size of the fine particles in the sample liquid can be electrically analyzed by measuring the size of the ionic current flowing between the first electrode 61 and the second electrode 62.

In the first microflow channel 21 and the second microflow channel 22, liquid introduction structure 90 explained in detail in the fourth embodiment is formed inside a reservoir 30 via liquid introduction inlet 40. In this manner, the present embodiment can realize a semiconductor microanalysis chip which can immediately introduce a sample liquid into a microflow channel 20, prevent the disconnection defect of the electrodes and relax restrictions on the electrode area while restraining the production cost.

Eighth Embodiment

Figure 12:
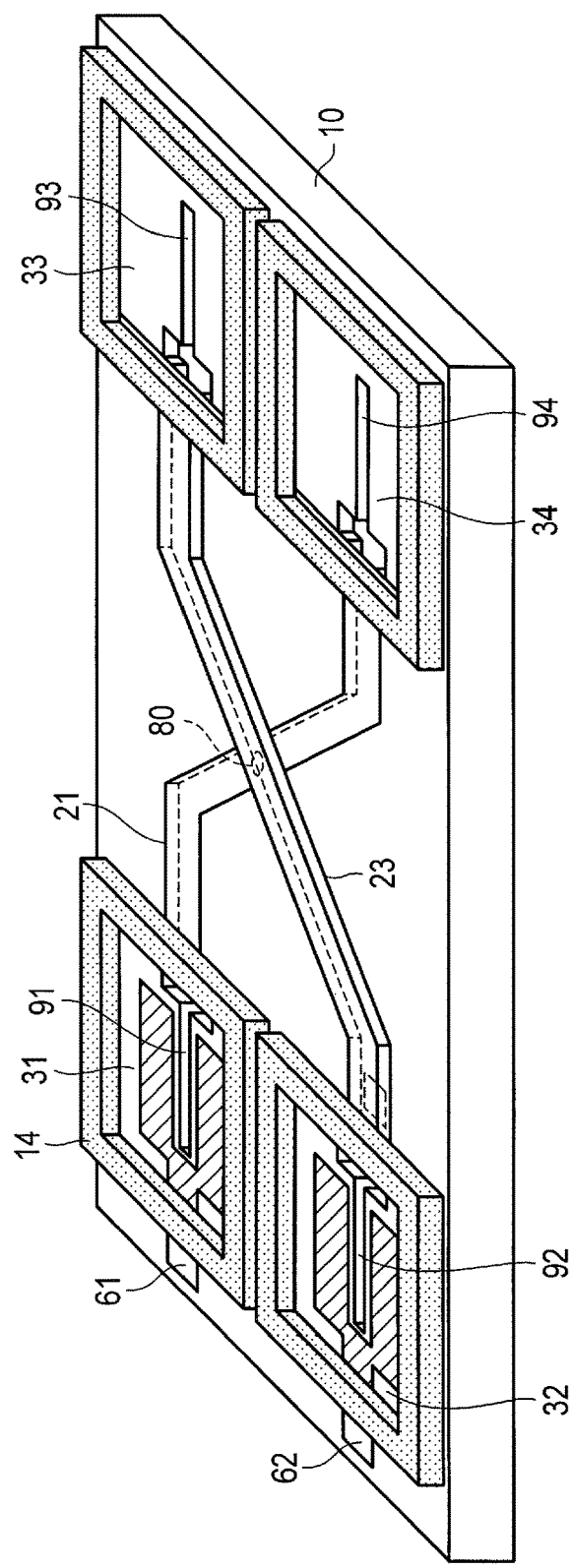
FIG. 12 is a perspective view showing the whole structure of a semiconductor microanalysis chip according to an eighth embodiment.
Figure 13:
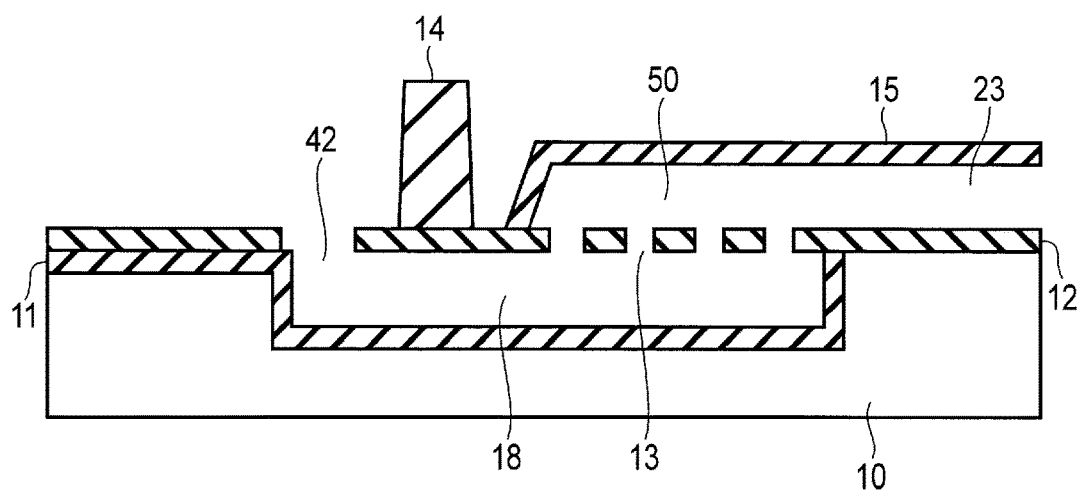
FIG. 13 is a cross-sectional view showing the main structure of the semiconductor microanalysis chip of FIG. 12.

FIG. 12 is a planar view showing the whole structure of a semiconductor microanalysis chip according to an eighth embodiment. FIG. 13 is a cross-sectional view showing the main structure of the microanalysis chip of FIG. 12. The elements identical to those of FIG. 8 and FIG. 11 are denoted by the same reference numbers as FIG. 8 and FIG. 11. Thus, the detailed explanation of such elements is omitted.

The present embodiment is different from the seventh embodiment explained above in respect that one of the microflow channels is formed in the shape of an insulating film tunnel.

A first microflow channel 21 has a substrate-excavating shape in a manner similar to the seventh embodiment. A second microflow channel 23 does not have a substrate-excavating shape. The second microflow channel 23 is a microflow channel formed in the shape of an insulating film tunnel comprising a hollow structure formed of an insulating film on a substrate 10. The second microflow channel 23 is not formed inside the substrate 10 and is formed on the substrate 10. Therefore, the second microflow channel 23 is positioned above the first microflow channel 21. The second microflow channel 23 intersects with the first microflow channel 21 in the central portion of the substrate 10. A micropore 80 for detection is formed in the intersecting portion.

To construct the second microflow channel 23, an insulating film is formed so as to cover a sacrificial layer after forming the pattern of the sacrificial layer on the substrate 10. Subsequently, the sacrificial layer is removed, thereby forming a channel having the shape of an insulating film tunnel. As shown in FIG. 13, the second microflow channel 23 is connected to a liquid introduction inlet 42 in a second reservoir 32 via a connecting passage 18 formed by excavating the substrate 10. A filter 50 may be formed in the portion connecting the connecting passage 18 and the second microflow channel 23. In a manner similar to the above, a connecting passage may be provided to connect a second microflow channel 22 and a third reservoir 33.

As explained above, in a manner similar to the third embodiment, the present embodiment comprises the second microflow channel 23 formed in the shape of an insulating film tunnel. Thus, the circular micropore 80 may be formed in the intersecting portion between the first and second microflow channels 21 and 23. In a manner similar to the third embodiment, the designing flexibility of the micropore 80 for fine particle inspection is high. Further, the inspection accuracy can be improved.

By forming the filter 50 in the portion connecting the connecting passage 18 and the second microflow channel 23, an effect similar to that of the first embodiment can be obtained.

Figure 14:
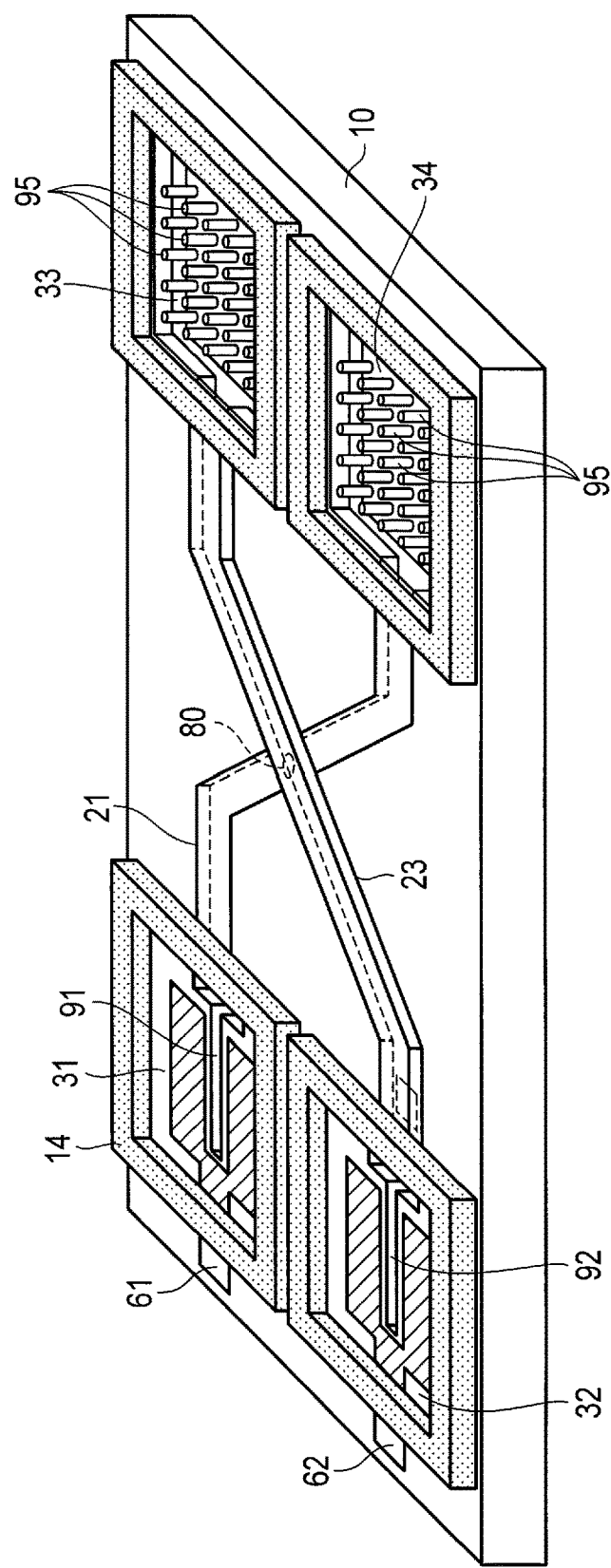
FIG. 14 is a perspective view showing a modification example of the semiconductor microanalysis chip of FIG. 12.

As explained in the seventh embodiment, there is no need to provide an electrode on the liquid discharging side. Thus, as shown in FIG. 14, a plurality of pillars may be provided on the discharging side. Specifically, pillars 95 formed by excavating the top surface of the substrate 10 may be provided in the third and fourth reservoirs 33 and 34. In this manner, it is possible to absorb and discharge a larger volume of liquid. Thus, the analysis time can be shortened.

Modification Example

The present invention is not limited to each of the above embodiments. The shape or the number of micropores for forming the filter provided in a liquid introduction inlet is not limited to the structure shown in FIG. 3 and may be appropriately modified in accordance with the specification. Further, the pattern of the liquid introduction inlet structure is not limited to the structure shown in FIG. 7, FIG. 9 or FIG. 10 and may be appropriately modified. The layout in a case where two flow channels are formed is not limited to the structure shown in FIG. 4 or FIG. 5 and may be appropriately modified in accordance with the specification.

The substrate is not limited to a semiconductor substrate and can be anything as long as the flow channels and the liquid introduction structures shown in the embodiments can be formed by an excavating process such as reactive etching.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A microanalysis chip comprising:
a substrate having a top surface;
a flow channel provided on a top surface side of the substrate and extending downward into the substrate, said flow channel being configured to have a sample liquid flow therethrough;
a bank formed on the top surface of the substrate and extending upward from the top surface of the substrate, said bank forming a wall enclosing an area of the top surface of the substrate; and
a reservoir for storing the sample liquid, the reservoir being formed by the wall of the bank and comprising:

a liquid introduction inlet provided on the top surface of the substrate in the bank for connection to an end of the flow channel, and a linear groove provided inside the bank at a bottom surface of the reservoir, the groove being connected to the liquid introduction inlet.

2. The chip of claim 1, wherein the flow channel is a flow channel in a trench shape provided on the top surface of the substrate, and the end of the flow channel is connected to the liquid introduction inlet.

3. The chip of claim 1, wherein the flow channel is provided on the top surface of the substrate in a tunnel shape by an insulating film, and the end of the flow channel is connected to the liquid introduction inlet via a connecting passage in a trench shape provided on the top surface of the substrate.

4. The chip of claim 1, further comprising an electrode which is provided in the reservoir, passes under the bank and extends to outside of the reservoir.

5. The chip of claim 1, wherein the groove is narrower than the liquid introduction inlet in width.

6. The chip of claim 1, wherein two or more flow channels are provided adjacent to each other, and one of a micro slit for fine particle detection and a micropore for fine particle detection is provided in an adjacent wall of each of the flow channels.

* * * * *